United States Patent

Grollier et al.

[11] 4,208,183
[45] Jun. 17, 1980

[54] PROCESS FOR IMPROVING THE STORAGE STABILITY OF INDOLE DYESTUFFS

[75] Inventors: Jean F. Grollier; Chantal Fourcadier, both of Paris, France

[73] Assignee: L'Oreal, Paris, France

[21] Appl. No.: 904,309

[22] Filed: May 9, 1978

[30] Foreign Application Priority Data

May 10, 1977 [FR] France ................................ 77 14254

[51] Int. Cl.$^2$ .............................................. A61K 7/13
[52] U.S. Cl. .......................................... 8/409; 8/609; 8/611
[58] Field of Search ...................... 8/10, 10.1, 10.2, 11, 8/32, 93

[56] References Cited

U.S. PATENT DOCUMENTS

| 3,194,734 | 7/1965 | Seemuller et al. ...................... 8/10.2 |
| 4,013,404 | 3/1977 | Parent et al. ........................ 8/10.2 X |

Primary Examiner—Howard T. Mars
Assistant Examiner—Vera C. Clarke

Attorney, Agent, or Firm—Fleit & Jacobson

[57] ABSTRACT

The invention relates to storage-stable dyestuff solutions which can be mixed at the time of use with appropriate carriers.

These solutions comprise at least one dihydroxyindole of the formula:

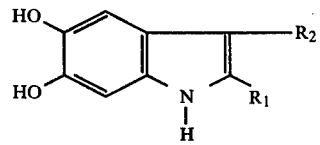

in which $R_1$ and $R_2$ independently of one another denote hydrogen or methyl, or a cosmetically acceptable salt thereof, in an anhydrous solvent chosen from amongst ethyl, isopropyl and tert.-butyl alcohol, ethylene glycol monomethyl, monoethyl and monobutyl ethers and the acetate of ethylene glycol monoethyl ether.

10 Claims, No Drawings

PROCESS FOR IMPROVING THE STORAGE STABILITY OF INDOLE DYESTUFFS

The present invention relates to solutions of indole dyestuffs. The invention more particularly relates to a process for preserving these dyestuffs in a liquid medium before they are introduced into dyeing compositions used for dyeing keratin fibres and, in particular, human hair.

The dyestuffs of the indole family, and in particular the 5,6-dihydroxyindoles, are well-known and have formed the subject of French Pat. Nos. 1,264,707, 1,133,594 and 1,166,172. However, it has been found that the commercial exploitation of these dyestuffs for hair dyeing presents numerous problems, especially because of their lack of stability during storage in the aqueous dyeing compositions usually employed for dyeing the hair.

Storage stability is known to be of great importance from the commercial point of view, mainly because it is sometimes necessary for the dyeing compositions to be stored for long periods of time and frequently under high ambient temperature conditions.

It has been suggested that the dyestuff can be preserved in the form of a powder which would only be mixed with the cosmetic carrier at the time of use, but the dyestuff gradually loses its solubility and its dyeing capacity if it is not preserved under very strict conditions.

We have now discovered that, in certain well-defined solvents, the 5,6-dihydroxyindoles preserve their dyeing capacity during storage.

The solutions which contain one or more 5,6-dihydroxyindoles correspond to the general formula:

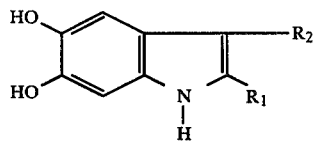

in which $R_1$ and $R_2$, which are identical or different, denote a hydrogen atom or a methyl group, or a cosmetically acceptable salt thereof, such as a halide and, in particular, the hydrobromide, in one or more anhydrous solvents chosen from ethyl alcohol, isopropyl alcohol and tert.-butyl alcohol, ethylene glycol monomethyl, monoethyl and monobutyl ethers and the acetate of ethylene glycol monoethyl ether.

Amongst these solutions, those in ethyl alcohol, ethylene glycol monoethyl ether, ethylene glycol monobutyl ether and the acetate of ethylene glycol monoethyl ether are particularly preferred.

The dyestuff as defined above is suitably present in the solution in an amount from 0.1 to 80%, and preferably from 5 to 50%, by weight. The concentration can be adjusted, according to the shades which it is desired to obtain, when the solution is used in the preparation of a composition intended for coloring the hair.

The present invention also provides a process for preserving a dyestuff of formula (I) which consists in storing the dyestuff, immediately after it has been synthesized, in one or more of the solvents defined above, preferably in the above-mentioned amounts.

Thus, it has been found that the dyestuff stored in the above-mentioned solvents retains its dyeing capacity for a substantially longer time than was possible to when this same dyestuff was stored in dyeing compositions which were ready to be applied to the hair.

The present invention also provides a process for the preparation of a dyeing composition intended to be applied directly to the hair which comprises introducing a dyestuff solution of this invention into a cosmetically acceptable carrier usually employed in hair dyeing.

The cosmetic carriers which can be used according to the invention can be in the form of creams, thickened gels or liquids, emulsions or simple lotions.

When these carriers are in the form of a cream, they generally comprise soaps or fatty alcohols in the presence of emulsifiers.

The soaps are typically formed from natural or synthetic fatty acids having 12 to 18 carbon atoms, such as lauric acid, myristic acid, palmitic acid and stearic acid, suitably at concentrations from 10 to 30% by weight with alkalizing agents such as sodium hydroxide, potassium hydroxide, ammonia, monoethanolamine, diethanolamine or triethanolamine.

These creams can contain, in addition to the soaps, adjuvants such as fatty amides and fatty alcohols.

Typical fatty amides include the mono- or di-ethanolamides of acids derived from copra, of lauric acid, of oleic acid or of stearic acid, and are preferably used at concentrations of up to 10% by weight.

Amongst the fatty alcohols, oleyl, myristyl, cetyl, stearyl and isostearyl alcohols can be used, in particular at concentrations of up to 10% by weight.

The creams can also be formulated from natural or synthetic alcohols having 12 to 18 carbon atoms, which are mixed with emulsifiers.

Typical alcohols include lauryl alcohol, myristyl alcohol, cetyl alcohol, stearyl alcohol, cetyl/stearyl alcohol and hydroxystearyl alcohol, generally used in an amount from 3 to 25% by weight.

The emulsifiers may be, for example, polyoxyethyleneated or polyglycerolated fatty alcohols such as a polyoxyethyleneated oleyl alcohol containing from 10 to 30 mols of ethylene oxide, stearyl alcohol containing 10 to 15 or 20 mols of ethylene oxide, polyglycerolated oleyl alcohol containing 4 mols of glycerol and polyoxyethyleneated synthetic $C_9$–$C_{15}$ fatty alcohols containing 5 to 10 mols of ethylene oxide. These "non-ionic" emulsifiers are generally present in an amount of 5 to 25% by weight.

Other emulsifiers which can be used include alkyl-sulphates, which may or may not be oxyethyleneated, such as sodium lauryl-sulphate, ammonium lauryl-sulphate, sodium cetyl-/stearyl-sulphate, triethanolamine cetyl-/stearyl-sulphate, mono- or tri-ethanolamine lauryl-sulphate, the sodium salt of the sulphate half-ester of lauryl alcohol which has been polyoxyethyleneated (with, for example, 2.2 mols of ethylene oxide) and the monoethanolamine salt of the sulphate half-ester of lauryl alcohol which has been oxyethyleneated (with, for example, 2.2 mols of ethylene oxide). These constituents are generally present at concentrations of 3 to 15% by weight.

When the cosmetic carriers used according to the invention are in the form of thickened gels or liquids, they either contain thickeners, which may or may not be in the presence of organic solvents, or they contain polyoxyethyleneated or polyglycerolated non-ionic compounds which may or may not be mixed with solvents.

Typical thickeners include sodium alginate or gum arabic, or cellulose derivatives such as methylcellulose, hydroxymethylcellulose, hydroxyethylcellulose, hydroxypropylcellulose, hydroxypropylmethylcellulose or carboxymethylcellulose, or carboxyvinyl polymers such as the Carbopols. The lotions can also be thickened using a mixture of polyethylene glycols and stearates or distearates of polyethylene glycols, or a mixture of amides and phosphoric acid esters.

The concentration of thickener is generally from 0.5 to 30%, and preferably from 0.5 to 15%, by weight.

They can also contain a surface-active agent in order to impart foaming and detergent properties to these carriers.

The carriers which are in the form of a gel can contain oxyethyleneated or polyglycerolated non-ionic compounds, typically at concentrations of 1 to 60% by weight optionally mixed with up to 30% by weight of solvent.

Amongst the polyoxyethyleneated or polyglycerolated non-ionic compounds, there may be mentioned, in particular, polyoxyethyleneated nonylphenol containing 4 or 9 mols of ethylene oxide, polyglycerolated oleyl alcohol containing 2 or 4 mols of glycerol, polyglycerolated cetyl/stearyl alcohol containing 2 or 6 mols of glycerol and polyoxyethyleneated synthetic fatty alcohols having 11 to 15 carbon atoms and containing from 3 to 10 mols of ethylene oxide. The gels can also be obtained from soaps of liquid fatty acids such as oleic or isostearic acid.

Amongst the solvents which can be used in this type of carrier, there may be mentioned, in particular, lower (i.e. of 1 to 6 carbon atoms) aliphatic alcohols such as ethyl alcohol or propyl or isopropyl alcohol, and glycols such as propylene glycol, butylglycol or ethylglycol.

These carriers can also contain adjuvants such as fatty amides. The latter can be the same as those listed above for the creams.

When the carriers are in the form of emulsions, they can be non-ionic or anionic. The non-ionic emulsions are formed from a mixture of oils and/or waxes, fatty alcohols, and polyoxyethyleneated fatty alcohols such as polyoxyethyleneated stearyl or cetyl/stearyl alcohols. Cations can be added to these compositions.

The anionic emulsions are usually formed from soaps; examples include the emulsion comprising self-emulsifying glycerol stearate and sold under the name IMWITOR 960 K by Messrs. DYNAMIT NOBEL, and the emulsions comprising a combination of glycerol monostearate with citric acid esters or with fatty alcohols and lipopeptides or with alkali metal stearates and sold under the names Lameform ZEM, LPM and NSM, respectively, by Messrs. GRUNAU.

When the carriers are in the form of lotions, they generally comprise water or aqueous solutions to which solvents and/or treatment products of cationic character, such as cations or cationic polymers which are usually employed in hair cosmetics, are optionally added.

Quaternary ammonium salts such as trimethylcetylammonium bromide and cetylpyridinium bromide can be used as cations.

The following may be mentioned as typical cationic polymers: quaternary vinylpyrrolidone copolymers such as the polymers sold under the name GAFQUAT 734, having a molecular weight of 100,000, and GAFQUAT 755, having a molecular weight of 1,000,000, by Messrs. GENERAL ANILINE, quaternary derivatives of cellulose ether such as those sold under the name JR 125, JR 400 and JR 30 M by Messrs. UNION CARBIDE, the quaternized polymers described in French Patent Applications Nos. 75/15162 and 76/20261, and soluble crosslinked polyamino-amides such as those described in French Patent Application No. 2,252,840 or in French Patent No. 1,583,363.

The polymer concentrations are generally 0.1 to 5% and preferably 0.1 to 3%, by weight.

The solvents can be low molecular weight alcohols having 1 to 4 carbon atoms or glycols such as those mentioned above. The solvent concentrations are generally up to 50% by weight.

All these carriers can contain additives which are usually employed in hair cosmetics, such as sunlight filters, optical brighteners, antioxidants, sequestering or complexing agents and perfumes.

The following may be mentioned by way of example: benzylidene-camphor as sunlight filter, sodium bisulphite and thioglycolic or thiolactic acids and their salts as antioxidants, ethylenediaminetetraacetic acid or diethylenetriaminepentaacetic acid and their salts as complexing agent.

The pH can be adjusted with alkaline agents such as mono- or tri-ethanolamine, ammonia, ammonium carbonate, potassium carbonate or sodium carbonate or sodium hydroxide, or with acidifying agents such as phosphoric, hydrochloric, tartaric, acetic, lactic or citric acid. It is generally from 3 to 12 and preferably from 5 to 10.

The amount of dyestuff solution containing dyestuffs relative to the cosmetic carrier is generally 1 to 80%, and preferably 3 to 50%, by weight.

The storage and subsequent mixing can be carried out in various ways using known devices, such as devices possessing two compartments, one of which contains the dyestuff solution and the other of which contains the cosmetic carrier.

A preferred method of carrying out the invention consists in using an aerosol device with a double compartment, the solvent phase containing the said dyestuffs and the aqueous phase forming the carrier being mixed by means of the valve. The propellants used in the said aerosols can be, in particular, carbon dioxide gas, nitrogen, nitrous oxide, volatile hydrocarbons such as butane, isobutane and propane, and halogenohydrocarbons such as methylene chloride or, preferably, fluorohydrocarbons (sold under the name Freon by Messrs. DU PONT DE NEMOURS), in particular fluorochlorohydrocarbons such as dichlorodifluoromethane (Freon 12), dichlorotetrafluoroethane (Freon 14) and trichloromonofluoromethane (Freon 11), chlorodifluoromethane (Freon 22), 1-chloro-1,1-difluoroethane (Freon 142 B) and 1-monochloro-2,2,2-trifluoroethane (Freon 133 A). These propellants can be used by themselves or in combination; a mixture of Freon 114/12, in proportions varying from 40:60 to 80:20, can be used in particular.

Suitable devices which can be used include those described in, inter alia, French Pat. No. 1,557,740, and French Patent Application Nos. 73/46537, 71/08902, 72/02321 and 76/05827. There may be mentioned, in particular, the plugs having a cavity of the sliding cap type containing the solution which is to be mixed with the carrier inside the flask carrying the plug, or an unpressurized container possessing at least one dispensing orifice in its outer casing, the said outer casing being elongate and made of deformable flexible material and enclosing at least one closed, brittle, rigid tube, the cosmetic carrier being situated outside the above-mentioned brittle tube and inside the flexible envelope and the dyestuff solution according to the invention being situated inside the rigid brittle tube.

A further example of a device which makes it possible to carry out the invention is a flask containing the cosmetic carrier and possessing a chamber having a diaphragm, which chamber is located inside the neck of the flask and contains the dyestuff solution. In this case, mixing is carried out when a trocar, which is held by a rim against the extreme outer edge of the neck of the said flask, slides and perforates the diaphragm and the bottom of the chamber.

The compositions prepared by introducing dyestuff solutions according to the present invention into the cosmetic carriers can be used for dyeing the hair essentially in accordance with two processes using either development of the coloration due to the effect of the air or development by means of an oxidizing agent.

In the dyeing process using development in air, the dyestuff solution mixed with the carrier is applied to the hair for, say, 5 to 30 minutes and is then rinsed out; the coloration is developed by oxidation in the air.

In the dyeing process using development by means of an oxidizing agent, an oxidizing agent, as a powder or in solution, is mixed with the carrier to which the dyestuffs solution defined above has been added, and the composition is applied to the hair by following the above procedure. The oxidizing agent, as a powder or in solution, can also be applied in a second stage after application to the hair of the dyeing composition prepared as indicated above, and after rinsing.

Suitable oxidizing agents are hydrogen peroxide, urea peroxide, persalts such as ammonium persulphate, sodium persulphate or potassium persulphate, barium peroxide and silver carbonate.

Stabilized oxidizing solutions can be in various forms, for example creams, thickened gels or liquids, emulsions or simple lotions.

Oxidizing agents which decompose in water should either be used in powder form or dissolved at the time of use.

The concentrations of oxidizing agent is generally from 0.1 to 6% by weight.

The compositions of this invention can be applied to any type of hair, that is to say natural hair, permed hair or hair which has been more or less bleached.

The following Examples further illustrate the present invention.

Tables I to V illustrate compositions according to the invention and their method of use.

Initially, dyestuff solutions indicated in Table I are prepared by mixing the dyestuff and the solvent which is substantially anhydrous, this Table showing the nature and amount of the dyestuff, the solvent and the amount of solvent.

When it has been prepared, the solution is stored for the lengths of time shown in Table I and is then mixed with the various cosmetic carriers shown in Table I and explained in Table II.

When it has been prepared, the dyeing composition is applied to the head of hair, the initial color of which is indicated in Tables III and IV.

Unless an oxidizing solution is indicated in the Tables, the coloration is developed by oxidation in air.

Table III relates to a process of application in a single stage which consists in introducing an oxidizing solution, in the amounts shown in Table III, into the dyeing compositions shown in Table I, and applying the composition thus prepared to the hair for the periods of time indicated. This Table indicates the color of the hair which has been treated and the shades obtained.

Table IV relates to a two-stage dyeing process which consists in applying the dyeing compositions defined in Table I for the periods of time shown, and applying, after rinsing, an oxidizing solution of the type, and in the amounts, shown in Table IV with reference to the particulars given in Table V.

The shades obtained are observed after rinsing, shampooing if desired, and drying.

The reference S indicates that the hair has been shampooed and the reference R indicates that it has only been rinsed.

TABLE I

PREPARATION OF THE DYEING COMPOSITIONS

| Examples | Dyestuffs | g % | Solvent | g | Storage time | Amount used (g) | Nature | Amount (g) |
|---|---|---|---|---|---|---|---|---|
| | | | | | | | Cosmetic carrier | |
| $S_1$ | 5,6-Dihydroxyindole | 16.5 | Ethylglycol qsp | 100 | 8 months | 2.5 | A | 37.5 |
| | 2,3-Dimethyl-5,6-dihydroxy-indole hydrobromide | 2 | | | | | | |
| $S_2$ | 5,6-Dihydroxyindole- | 28.6 | Ethylglycol Butylglycol qsp | 50 100 | 6 months | 2.8 | B | 17.2 |
| $S_3$ | 2,3-Dimethyl-5,6-dihydroxy-indole | 5 | Ethylglycol Ethylglycol acetate qsp | 10 100 | 12 months | 8 | C | 32 |
| $S_4$ | 2,3-Dimethyl-5,6-dihydroxy-indole hydrobromide | 30 | Butylglycol Ethanol qsp | 35 100 | 6 months | 5 | D | 15 |
| $S_5$ | 5,6-Dihydroxyindole | 50 | Butylglycol Ethanol qsp | 40 100 | 16 months | 1.6 | E | 38.4 |
| $S_6$ | 5,6-Dihydroxyindole | 30 | Ethylglycol Ethanol qsp | 20 100 | 10 months | 1.25 | F | 18.75 |
| | 2,3-Dimethyl-5,6-dihydroxy-indole | 2 | | | | | | |
| $S_7$ | 2-Methyl-5,6-dihydroxy-indole | 10 | Ethylglycol | 30 | 6 months | 2.5 | G | 17.5 |
| | 2,3-Dimethyl-5,6-dihydroxy-indole hydrobromide | 30 | Ethanol qsp | 100 | | | | |

TABLE I-continued
PREPARATION OF THE DYEING COMPOSITIONS

| | Dyestuff solution | | | | | | Cosmetic carrier | |
|---|---|---|---|---|---|---|---|---|
| | Preparation | | | | Storage | Amount | | Amount |
| Examples | Dyestuffs | g % | Solvent | g | time | used (g) | Nature | (g) |
| $S_8$ | 5,6-Dihydroxyindole | 25.5 | Ethylglycol | 35 | 1 year | 2.75 | A | 37.25 |
| | 2-Methyl-5,6-dihydroxy-indole | 1.5 | Ethanol qsp | 100 | | | | |
| $S_9$ | 5,6-Dihydroxyindole | 9 | | | | 4.4 | H | 35.6 |
| | 2,3-Dimethyl-5,6-dihydroxyindole | 1 | Ethylglycol qsp | 100 | 1 year | | | |
| $S_{10}$ | 5,6-Dihydroxyindole | 20 | Butylglycol qsp | 100 | 24 hours | 4 | H | 36 |
| $S_{11}$ | 5,6-Dihydroxyindole | 10 | | | | 4 | I | 36 |
| | 2,3-Dimethyl-5,6-dihydroxyindole hydrobromide | 2.5 | Ethylglycol qsp | 100 | 4 months | | | |
| $S_{12}$ | 5,6-Dihydroxyindole | 45 | Butylglycol | 30 | 12 months | 1.25 | J | 38.2 |
| | | | Ethanol qsp | 100 | | | | |
| $S_{13}$ | 5,6-Dihydroxyindole | 19 | Butylglycol qsp | 100 | 18 months | 4 | K | 36 |
| $S_{14}$ | 5,6-Dihydroxyindole | 20 | Ethylglycol qsp | 100 | 9 months | 2 | M | 18 |

TABLE II
EXAMPLES OF CARRIERS

| Constituents | Carrier A | Carrier B | Carrier C |
|---|---|---|---|
| Copra diethanolamide sold under the name "COMPERLAN KD" by Messrs. DEHYDAG | 5.3 g | 11.6 g | 5 g |
| Hydroxymethylpropylcellulose sold under the name "METHOCEL F 4 M" by Messrs. DOW CHEMICAL | 1.1 g | 2.3 g | 1.5 g |
| Sodium lauryl-sulphate containing 2 mols of ethylene oxide, sold under the name "DELF 8533" by Messrs. ASTRA CALVE | | | 10 g |
| Sodium bisulphite | 1 cc | | |
| Urea | | | 7.5 g |
| Monoethanolamine | 3 g | | |
| Triethanolamine | | 7 g | |
| Water | qsp 100 g | qsp 100 g | qsp 100 g |

| Constituents | Carrier D | Carrier L |
|---|---|---|
| Polyoxyethyleneated nonylphenol containing 4 mols of ethylene oxide, sold under the name "REMCOPAL 334" by Messrs. GUERLAND | 40 g | 22 g |
| Polyoxyethyleneated nonylphenol containing 9 mols of ethylene oxide, sold under the name "REMCOPAL 349" by Messrs. GUERLAND | 18.5 g | 22 g |
| EDTA sold under the name "DISSOLVINE Z" by Messrs. NOURY FRANCE | | 0.4 g |
| Butylglycol | | 8 g |
| Propylene glycol | | 8 g |
| 40% Strength solution of DTPA in water, sold under the name "MASQUOL DTPA" by Messrs. PROTEX | 6.5 g | |
| Sodium bisulphite | | 1 cc |
| 22° Baume strength ammonia solution | 10.5 cc | 10 cc |
| Water | qsp 100 g | qsp 100 g |

| Constituents | Carrier E | Carrier F | Carrier G | Carrier K |
|---|---|---|---|---|
| 50/50 Cetyl/stearyl alcohol sold under the name "LANETTE WAX 0" by Messrs. DEHYDAG | 8 g | 16 g | 16 g | 8 g |
| Oleyl alcohol | 1.35 g | 2.7 g | 2.7 g | 1.35 g |
| Tertiary fatty amine sold under the name "CEMULCAT OS 12" by Messrs. RHONE POULENC Industries | 1.6 g | 3.2 g | 3.2 g | 1.6 g |
| Ammonium lauryl-sulphate containing 20% of fatty acid, sold under the name "SIPON LA 30" by Messrs. HENKEL | 5.5 g | 11 g | 11 g | 5.5 g |
| 40% Strength solution of DTPA in water, sold under the name "MASQUOL DTPA" by Messrs. PROTEX | | 4.4 g | 4.4 g | 1 g |
| Sodium bisulphite | | | | 1 cc |
| Monoethanolamine | 2.9 g | | | |
| Triethanolamine | | | 6 g | 3 g |
| 22° Baume strength ammonia solution | | | 2.5 cc | |
| Water | qsp 100 g | qsp 100 g | qsp 100 g | qsp 100 g |

| Constituents | Carrier H | Carrier I |
|---|---|---|

TABLE II-continued
EXAMPLES OF CARRIERS

| | | |
|---|---|---|
| 16% Strength hydroxyethylcellulose sold under the name "CELLOSIZE WP 3" by Messrs. CARBIDE & CARBONI | 34 g | 34 g |
| 40% Strength solution of DTPA in water, sold under the name of "MASQUOL DTPA" by Messrs. PROTEX | | 1.1 g |
| Sodium bisulphite | 1 cc | |
| Pure lactic acid q.s.p. | | pH 6 |
| Water | qsp 100 g | qsp 100 g |

| Constituents | Carrier J |
|---|---|
| Partially oxyethyleneated self-emulsifying non-ionic wax sold under the name "SINNOWAX OD" by Messrs. SINNOVA | 2 g |
| Cocoa monoethanolamide | 0.6 g |
| Trimethylcetylammonium bromide | 0.1 g |
| Triethanolamine | 2.9 g |
| Water | qsp 100 g |

| | Carrier M |
|---|---|
| Quaternized vinylpyrrolidone copolymer having a molecular weight of 1,000,000, marketed under the name GAFQUAT 755 by Messrs. GENERAL ANILINE | 0.5 g |
| Quaternized cellulose sold under the name JR 400 by Messrs. UNION CARBIDE | 0.5 g |
| Quaternized polymer having the formula: $$\left[ \begin{array}{cc} CH_3Cl^- & CH_3Cl^- \\ N^+-(CH_2)_3-N^+-(CH_2)_6 \\ CH_3 & CH_3 \end{array} \right]_n$$ | 0.3 g |
| Water q.s.p. pH adjusted to 6. | 100 g |

TABLE III
APPLICATION TO HAIR DYEING

| Examples | Dyeing composition | Oxidizing solution introduced into the dyeing composition Nature | g | Application Time (of application) minutes | Post-treatment | Head of hair | Shades obtained |
|---|---|---|---|---|---|---|---|
| 1 | S₁ | | | 15 | S | Light chestnut containing a high percentage of white hair | Light grey concealing white hair |
| 2 | S₂ | hydrogen peroxide of 10 volumes strength | 20 | 20 | R | Blond containing 80% of white hair | Uniform blond |
| 3 | S₂ | urea peroxide (powder) | 1 | 20 | R | Blond containing 80% of white hair | Very luminous blond |
| 4 | S₃ | | | 20 | S | Light chestnut containing a high percentage of white hair | Golden chestnut |
| 5 | S₄ | hydrogen peroxide of 4 volumes strength | 20 | 30 | S | Blond containing a high percentage of white hair | Natural blond |
| 6 | S₅ | | | 20 | S | White | Light chestnut |
| 7 | S₆ | hydrogen peroxide of 2 volumes strength | 20 | 20 | S | Deep chestnut containing 60% of white hair and bleached beforehand | Chestnut |
| 8 | S₇ | hydrogen peroxide of 4 volumes strength | 20 | 30 | S | Blond hair containing a high percentage of white hair | Deep blond with a red sheen |

TABLE IV
TWO-STAGE DYEING PROCESS

Oxidizing solution applied to the head of hair

Time (of

TABLE IV-continued

| Examples | Dyeing composition | Application time minutes | Head of hair treated | Nature | application) minutes | Post-treatment | Shades obtained |
|---|---|---|---|---|---|---|---|
| 9 | $S_1$ | 15 | Light chestnut containing a high percentage of white hair | $O_1$ | 5 | S | Uniform light chestnut with a golden sheen |
| 10 | $S_8$ | 15 | Chestnut containing a high percentage of white hair and bleached beforehand | $O_1$ | 5 | R | Chestnut with an auburn sheen |
| 11 | $S_9$ | 15 | White | $O_3$ | 10 | S | Ashen deep grey |
|  |  |  |  |  | 15 | S | Golden grey |
| 12 | $S_{10}$ | 20 | Deep blond containing 90% of white hair | $O_2$ | 10 | S | Ashen deep blond |
| 13 | $S_{11}$ | 15 | Chestnut containing a high percentage of white hair and bleached beforehand in two tones | $O_4$ | 10 | S | Natural deep blond with a good covering of white hair |

| Examples | Dyeing composition | Application time minutes | Head of hair treated | Oxidizing solution applied to the head of hair | | | Shades obtained |
|---|---|---|---|---|---|---|---|
|  |  |  |  | Nature | Time minutes | Post-treatment |  |
| 14 | $S_{12}$ | 15 | Chestnut with a high percentage of white hair | $O_1$ | 5 | S | Luminous copper chestnut with a good covering of white hair |
| 15 | $S_{13}$ | 20 | White hair permed beforehand | $O_2$ | 5 to 25 | S | Natural blond to natural chestnut |
| 16 | $S_{15}$ | 5 | Blond containing a high percentage of white hair | hydrogen peroxide of 10 volumes strength | 5 | R | Uniform ashen blond |

EXAMPLE 17

A dyestuff solution is prepared by mixing 9 g of 5,6-dihydroxyindole with ethanol which is present in a sufficient amount to make up 100 g.

After storing the said solution for 8 months, 4 g of this solution are mixed, at the time of use, with 36 g of the cosmetic carrier K defined in Table II.

This dyeing composition is applied for 20 minutes to a light chestnut head of hair containing a high percentage of white hair and is then rinsed out.

40 g of the composition obtained by mixing, weight for weight, the carrier L defined in Table II and an oxidizing solution indicated in Tables III to V are then applied for 15 minutes.

After rinsing, shampooing and drying, the following colorations are obtained, depending on the oxidizing solution chosen: very natural chestnut, using hydrogen peroxide of 2 volumes strength as the oxidizing solution, and restrained ashen chestnut, using a 1% strength by weight solution of ammonium persulphate.

TABLE V

| Constituents | OXIDIZING SOLUTIONS | | | |
|---|---|---|---|---|
|  | $O_1$ | $O_2$ | $O_3$ | $O_4$ |
| Silver carbonate | 0.3 g |  |  |  |
| Hydrogen peroxide of 20 volumes strength |  | 15 g | 5 g |  |
| Powdered barium peroxide |  |  |  | 1 g |
| Olein | 2 g |  |  |  |
| Ethanol | 4 g |  |  |  |
| 40% strength solution of DTPA in Water, sold under the name "MASQUOL DTPA" by Messrs. PROTEX |  | 1 g | 1 g |  |
| Monoethanolamine |  | 5 g |  |  |
| 21° Baume strength ammonia solution | 2.9 cc |  | 5 cc | 5 cc |
| Water q.s.p. | 100 g | 100 g | 100 g | 100 g |

We claim:

1. A process for improving the storage stability of either a dye having the formula:

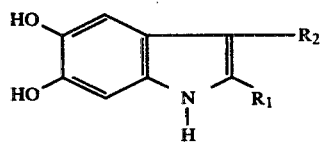

in which $R_1$ and $R_2$, identical or different, are hydrogen or methyl, or a cosmetically acceptable salt of said dye comprising the steps of dissolving at least one of said dye or salt thereof in at least one substantially anhydrous hydroxylic solvent selected from the group consisting of ethyl alcohol, isopropyl alcohol, tert.-butyl alcohol, ethylene glycol monomethyl ether, ethylene glycol monoethyl ether, ethylene glycol monobutyl ether, and the acetate of ethylene glycol monoethyl ether, wherein the dye or salt thereof is present in an amount from about 0.1 to 80% by weight, and maintaining said dye in the presence of said anhydrous solvent during storage.

2. The process of claim 1, wherein the dye is in the form of a halide.

3. The process of claim 1, wherein the dye is in the form of a hydrobromide.

4. The process of claim 1, wherein the dye is 5,6-dihydroxyindole.

5. The process of claim 3, wherein the dye is 2,3-dimethyl-5,6-dihydroxyindole hydrobromide.

6. The process of claim 1, wherein the dye is 2,3-dimethyl-5,6-dihydroxyindole.

7. The process of claim 1, wherein the anhydrous solvent is ethyl alcohol.

8. The process of claim 1, wherein the dye is present in an amount from 0.5 to 50% by weight.

9. The process of claim 1, wherein the dye is 2-methyl-5,6 dihydroxyindole.

10. The process of claim 1, wherein the anhydrous solvent is selected from the group consisting of ethylene glycol monoethyl ether, ethylene glycol monobutyl ether and the acetate of ethylene glycol monoethyl ether.

* * * * *